United States Patent
Allen, III

(10) Patent No.: US 8,057,381 B2
(45) Date of Patent: Nov. 15, 2011

(54) METHOD AND IMPLANT MATERIAL FOR TREATMENT OF URINARY INCONTINENCE

(76) Inventor: William F Allen, III, Atlanta, GA (US)

( * ) Notice: Subject to any disclaimer, the term of this patent is extended or adjusted under 35 U.S.C. 154(b) by 1247 days.

(21) Appl. No.: 11/735,779

(22) Filed: Apr. 16, 2007

(65) Prior Publication Data
US 2008/0254097 A1 Oct. 16, 2008

(51) Int. Cl.
A61F 2/02 (2006.01)
(52) U.S. Cl. .......................................... 600/30; 424/430
(58) Field of Classification Search .............. 600/29–32, 600/37; 424/430–433
See application file for complete search history.

(56) References Cited

U.S. PATENT DOCUMENTS

| | | |
|---|---|---|
| 4,969,474 A | 11/1990 | Schwarz |
| 5,336,263 A | 8/1994 | Ersek et al. |
| 5,746,222 A | 5/1998 | Simon et al. |
| 5,755,658 A | 5/1998 | Wallace et al. |
| 6,296,607 B1 | 10/2001 | Milbocker |
| 6,685,626 B2 | 2/2004 | Wironen |
| 6,830,052 B2 | 12/2004 | Carter et al. |
| 2002/0107429 A1 | 8/2002 | Wironen |
| 2002/0161382 A1 | 10/2002 | Neisz et al. |
| 2005/0069591 A1 | 3/2005 | Bernstein et al. |
| 2005/0261258 A1 | 11/2005 | Kolodney et al. |
| 2005/0267080 A1 | 12/2005 | Kolodney et al. |
| 2006/0127468 A1 | 6/2006 | Kolodney et al. |
| 2006/0154906 A1 | 7/2006 | Kolodney et al. |
| 2008/0318870 A1 | 12/2008 | Moriarty et al. |

OTHER PUBLICATIONS

Hannah et al., Extraperitoneal retropubic laparoscopic urethropexy, J Am Assoc Gynecol Laparasc, Feb. 2001, 8(1): 107-10.

Morley & Nethercliff, Minimally invasive surgical techniques for stress incontinence surgery, Best Pract Res Clin Obstet Gynaecol, Dec. 2005, 19(6): 925-40.
Rotunda et al., Detergent effects of sodium deoxycholate . . . , Dermatol Surg, Jul. 2004, 30(7): 1001-08.
Rotunda et al., Lipomas treated with subcutaneous deoxycholate injections, J Am Acad Dermatol, Dec. 2005, 53 (6): 973-78.
Rotunda & Kolodney, Mesotherapy and phosphatidylcholine injections: historical clarification and review, Dermatol Surg, Apr. 2006, 32(4): 465-80.
Norton & Brubaker, Urinary incontinence in women, Lancet, Jan. 2006, 367(9504): 57-67.
Nygaard & Heit, Stress urinary incontinence, Obstet Gynecol, Sep. 2004, 104(3): 607-20.
Leach et al., Female stress urinary incontinence clinical guidelines panel summary report . . . , J Urol, Sep. 1997, 158 (3 Pt 1): 875-80.
Macura et al., MR imaging of the female urethra and supporting ligaments in assessment of urinary incontinence, Radiographics, Jul.-Aug. 2006, 26(4): 1135-49.

(Continued)

*Primary Examiner* — Charles A Marmor, II
*Assistant Examiner* — Carrie R Dorna
(74) *Attorney, Agent, or Firm* — Sutherland Asbill & Brennan LLP

(57) ABSTRACT

Methods and implant materials are provided for treating urinary incontinence. The methods may include providing a composition that includes at least one pharmaceutically active formulation capable of retropubic fat dissolution; and introducing the composition into the retropubic space, preferably via a minimally invasive procedure, to contact adjacent tissue and promote dissolution of retropubic fat therein and consequent induction of adhesions. The implant material for treating urinary incontinence may include at least one pharmaceutically active detergent for promoting retropubic fat dissolution; and a biodegradable carrier material, wherein the implant material is sized and shaped for placement within a patient's retropubic space. The implant material may further include an auxiliary adhesion-promoting material.

20 Claims, 7 Drawing Sheets

Laparoscopic Insertion

OTHER PUBLICATIONS

Rose & Morgan, Histological changes associated with mesotharpy for fat dissolution, J Cosmet Laser Ther, Mar. 2005, 7(1): 17-19.

Hasengschwandtner, Phosphatidylcholine treatment to induce lipolysis, J Cosmet Dermatol, Dec. 2005, 4(4): 308-13.

Rittes et al., Injection of phosphatidylcholine in fat tissue: an experimental study of local action in rabits, Aesthetic Plast Surg, Jul.-Aug. 2006, 30(4): 474-78.

Rittes, The use of phosphatidylcholine for correction of localized fat deposits, Aesthetic Plast Surg, Jul.-Aug. 2003, 27 (4): 315-18.

Salles et al., Histologic response to injected phosphatidylcholine in fat tissue: experimental study in new rabbit model, Aesthetic Plast Surg, Jul.-Aug. 2006, 30(4): 479-84.

Hexsel et al., Phosphatidylcholine in the treatment of localized fat, J Drugs Dermatol, Oct. 2003, 2(5): 511-18.

Deng et al., Under-reporting of major complications of sling procedures, Abstracts of the American Urological Association Annual Meeting, J Urol, Apr. 2006, 175(4 Supp): 1-554.

Andonian et al., Randomized clinical trial comparing transobturator tape, prolen mesh sling, and tension-free vaginal tape, Abstracts of the American Urological Association Annual Meeting, J Urol, Apr. 2006, 175(4 Supp): 1-554.

O'Connor et al., Early outcomes of mid-urethral slings for femal stress urinary incontinence stratified by valsalva leak point pressure, Abstracts of the American Urological Association Annual Meeting, J Urol, Apr. 2006, 175(4 Supp): 1-554.

Blavias & Groutz, Urinary incontinence: pathophysiology, evaluation, and management overview. Campbell's Urology, 8th Ed., 2002: 1027-1052.

International Continence Society, Factsheet 3: Stress Urinary Incontinence, Jul. 2005.

Laparoscopic Insertion

Manual Insertion

Transabdominal Injection

Transvaginal Injection

METHOD AND IMPLANT MATERIAL FOR TREATMENT OF URINARY INCONTINENCE

BACKGROUND OF THE INVENTION

Urinary incontinence is a prevalent condition with significant social, economic, quality of life, and medical consequences. The reported prevalence has been variable depending upon the manner in which the problem has been defined. When referring to incontinence of any degree, an overall prevalence of 29 percent of women has been reported. Incontinence of severe degree was reported in 7 percent of women. Age is a significant factor with relatively few young women reporting daily leakage, but daily or severe leakage occurs in 10 percent of middle-aged women. Various classification schemes for urinary incontinence have been described, a non-limiting example of which includes the types of incontinence referred to as stress incontinence, urge incontinence, mixed incontinence, overflow incontinence, continuous incontinence, and situational incontinence.

A frequent clinical problem is the type of incontinence referred to as "stress urinary incontinence" or "stress incontinence." Stress incontinence has been described as the "involuntary leakage of urine on effort or exertion." It is the most common type of incontinence for which women seek the advice of a clinician. Causes of stress urinary incontinence include urethral hypermobility, intrinsic sphincter deficiency, and combinations thereof.

Urethral hypermobility involves the rotational descent of the bladder neck and proximal urethra during increases in abdominal pressure. Descent of these structures below the pelvic floor allows the disproportionate transfer of abdominal pressure to the bladder relative to the urethra. As the bladder pressure exceeds the urethral closure pressure, leakage ensues. Leakage will typically occur during physical activity such as coughing, sneezing, laughing, lifting, or exercise.

Intrinsic sphincter deficiency (ISD) denotes an intrinsic malfunction of the urethral sphincter, regardless of its position or descent during physical stress. Thus, the urethral closure pressure is inadequate to maintain continence even when the urethra is positioned appropriately. Conditions often associated with an increased risk of ISD include previous urethral or periurethral surgery, neurological problems, radiation, and estrogen deficiency.

Physical therapy has been recommended as a first line approach in the treatment of stress incontinence. When physical therapy has been unsuccessful, various surgical procedures have been employed. In recent decades, surgeons have based their recommendations regarding the most suitable type of surgical procedure on the distinctions between urethral hypermobility and intrinsic sphincter deficiency. It has been common practice to recommend a suspension procedure for the former and a sling or bulking procedure for the latter. More recently this approach has been called into question because many women have contributing components of both disorders.

Suspension techniques commonly used for the treatment of urethral hypermobility include the Marshall-Marchetti-Krantz procedure and the Burch procedure. The Marshall-Marchetti-Krantz (MMK) procedure suspends the bladder by placing sutures at the periosteum of the pubis or pubic symphysis. The Burch procedure achieves support by suturing to Cooper's ligament. Although cure rates of 80 percent have been reported, these procedures traditionally require open surgical exposure and hospitalization for recovery. The laparoscopic Burch procedure offers a minimally invasive approach; however, the effectiveness is less satisfactory.

Suburethral sling procedures also are used to treat incontinence. These procedures provide stabilization of urethral position and/or compression of the urethra by placing a strip of tissue or other material beneath the urethra. The strip of material has sometimes been described as a hammock or backboard. A compressive sling is required when urethral function is very poor. Autologous fascia has been used for this procedure, although xenografts (such as porcine dermis) and synthetic materials also have been used. There are concerns regarding both autologous and xenographic materials, however, with regard to durability. And there is the possibility of severe long-term complications from use of synthetic materials.

Another method of treatment commonly used for treating ISD involves the injection of bulking agents into the periurethral tissue. Various injectable substances have been used, including polytetrafluoroethylene (PTFE), collagen, silicone, and carbon coated beads; however, an ideal material has yet to be developed. Bovine collagen, generally recognized as the most widely used agent, has had disappointing long-term effectiveness, while use of PTFE has raised concerns about the unintended migration of non-degradable implanted particles to other parts of the body.

More recently, the TVT (Tension-free Vaginal Tape) procedure has become a popular treatment for stress incontinence. TVT procedures involve the implantation of a proprietary polypropylene mesh tape at the mid-urethral level. The simplicity of the implantation procedure allows the procedure to be done in a relatively short period of time on an outpatient basis. Although the initial reports indicate low rates of complications, recent reports indicate that complications with the TVT procedure have been significantly underreported. Notably, passage of the instruments and sling material through the retropubic space in close proximity to important anatomical structures is performed without visualization during the procedure, sometimes resulting in complications such as bladder perforation, major vascular injuries, bowel injury, and nerve entrapment. In addition, there is concern about the potential for developing long-term complications from the permanent and synthetic implant material in this location. Such complications may include urethral erosion, vaginal extrusion, and voiding dysfunction. Although the TVT procedure easily may stabilize a hypermobile urethra, it is important to weigh the convenience of the implantation procedure against both the risks of the procedure and the potential long-term complications that may arise from a permanent implant.

The TOT (trans-obturator tape) procedure recently has gained popularity as an alternative to the TVT procedure. This procedure involves the passage of a propylene mesh tape through the obturator membrane instead of the retropubic space to avoid some of the problems associated with the TVT procedure. There is a scarcity of data, however, regarding the long-term safety or effectiveness of this procedure. In addition, the occurrence of protracted upper leg pain has been reported as a troubling complication in some patients.

Thus, a need remains for improved techniques for treating stress urinary incontinence. It would be particularly desirable to provide methods and devices that are minimally invasive and provide long-term correction or continence improvement, while avoiding the use of permanent (e.g., non-degradable) implant structures.

SUMMARY OF THE INVENTION

Methods, compositions, and devices are provided for treating urinary incontinence in a patient. In one aspect, the method of treatment includes the steps of providing a composition including at least one pharmaceutically active formulation capable of retropubic fat dissolution; and introducing the composition into the retropubic space, to contact adjacent tissue and promote dissolution of retropubic fat therein. The dissolution of the retropubic fat may occur, for example, by the solubilization of fat molecules, destruction of fat cell membranes, or a combination thereof. In a preferred embodiment, the pharmaceutically active formulation induces the formation of adhesions in the retropubic space. Advantageously, the step of introducing at least one pharmaceutically active formulation into the retropubic space may be performed using a minimally invasive procedure.

In another aspect, implant materials are provided for treating urinary incontinence. The implant material includes at least one pharmaceutically active detergent for promoting retropubic fat dissolution and a biodegradable carrier material. The implant material is sized and shaped for placement within a patient's retropubic space.

In various embodiments, the biodegradable carrier material of the implant material may include woven or non-woven fibers, a monolithic structure, or an elastic sponge material. Examples of suitable biodegradable materials may include polymers selected from poly(lactic acid)s, poly(glycolic acid)s, poly(lactic-co-glycolic acid)s, poly(lactide-co-glycolide)s, polyethylene glycol copolymers, polyanhydrides, poly(ortho)esters, poly(butyric acid)s, poly(valeric acid)s, poly(lactide-co-caprolactone)s, and blends, and copolymers thereof. The pharmaceutically active formulation may be coated on the biodegradable carrier material, contained within the biodegradable carrier material, or dispersed within the biodegradable carrier material.

In a preferred embodiment, the pharmaceutically active formulation of the methods and implant materials described herein may include a pharmaceutically active detergent. Examples include ionic detergents, non-ionic detergents, zwitterionic detergents, bile acids, and combinations thereof. For example, the bile acid may be selected from deoxycholic acid, cholic acid, chenodeoxycholic acid, 7-alpha-dehydroxylate acid, chenodeoxycholic acid, lithocholic acid, ursodeoxycholic acid, dihydroxy-bile acids, trihydroxy-bile acids, and salts thereof. An example of an ionic detergent is sodium deoxycholate, and an example of a non-ionic detergent is alkylaryl polyethyl alcohol. An example of a zwitterionic detergent is lauryldimethylbentaine.

The pharmaceutically active detergent may include a phosphoglyceride. Examples of phosphoglycerides include phosphatidylcholines, phosphatidylethanolamines, phosphatidylserines, phospholipid ethers, phosphatidylinositols, phosphatidylglycerols, and combinations thereof.

The compositions and implant material may include additional components. For instance, the implant material/other composition useful in the treatment method may include an anti-inflammatory agent, an analgesic, a dispersing agent, a penetration enhancer, a pharmaceutically acceptable excipient, or a combination thereof. In one particular embodiment, the composition or implant material may include an auxiliary adhesion-promoting material selected from bone particles, hydroxyapatite particles, non-osteoinductive precipitated bone matrix (DBM) particles, collagen particles, insoluble salts, talc, cross-linked tissues, or a combination thereof.

DETAILED DESCRIPTION OF THE INVENTION

Figure 1:
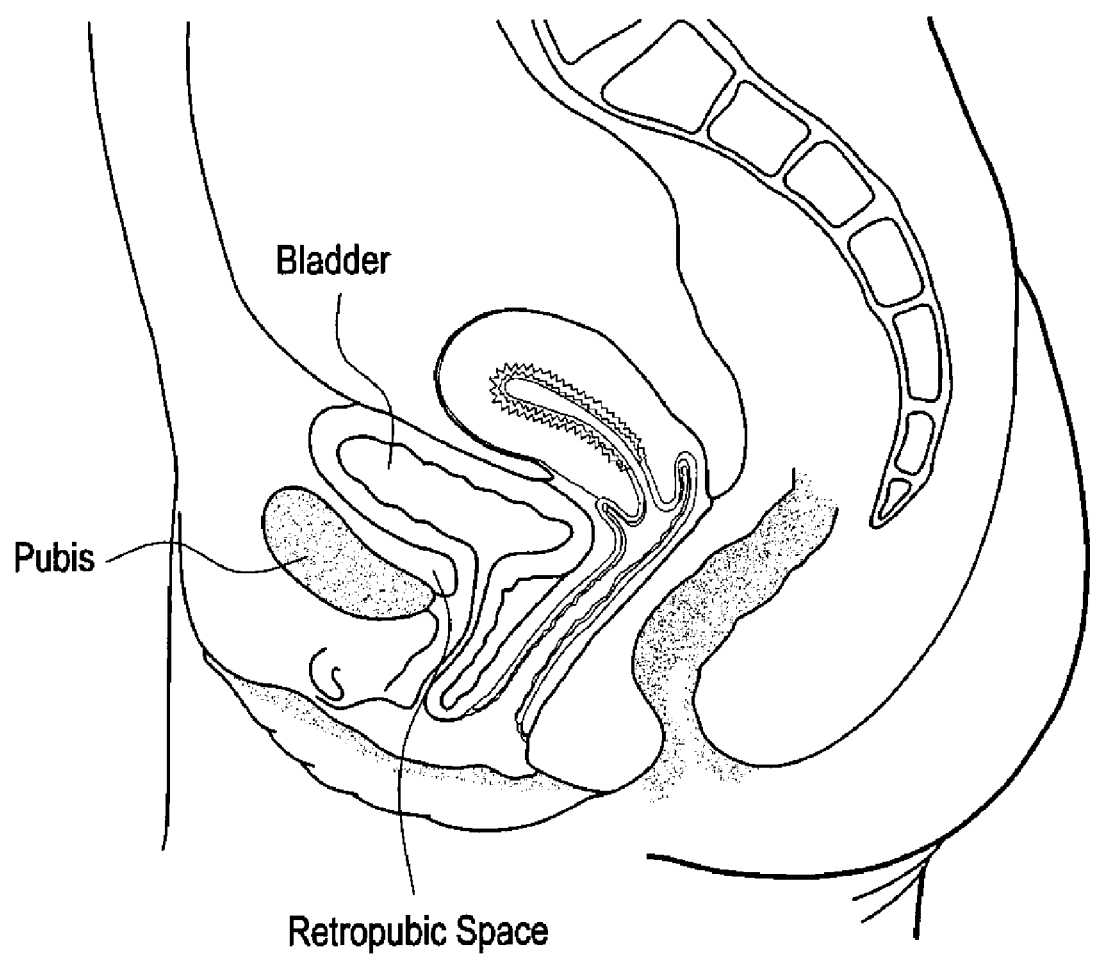
FIG. 1 is an illustration of the retropubic space as defined herein.

Methods, compositions, and devices are provided for the treatment of urinary incontinence by means of retropubic fat dissolution, by induction of adhesions in the retropubic space to stabilize the lower urinary tract, or by a combination thereof. Unlike sling materials and the artificial urinary sphincter, the techniques for treating urinary incontinence described herein are minimally invasive and should not require the use of a permanent implant to achieve long-term continence enhancement.

It generally is known that the physical characteristics of fat tissue include elasticity and deformability. Thus, the presence of fat tissue is a contributing factor to urethral hypermobility, one of the known causes of stress urinary incontinence. In addition, the presence of fat tissue between the urinary tract and more stable pelvic structures also may contribute to the failure of other treatments for hypermobility-associated incontinence, for example, by precluding adequate adhesion between the tissues following suturing techniques such as the MMK procedure, the Burch procedure, or the laparoscopic Burch procedure.

Studies have demonstrated by magnetic resonance imaging that enlargement of the retropubic space occurs in women with stress incontinence. The predominant component of this space is fat tissue. Conversely, it has been reported that weight loss improves continence (reduces incontinence) in overweight and obese women. The particular relationship between body weight and urinary incontinence is unknown; however, one possible mechanism may be related to increases in abdominal pressure and volume associated with increased body fat. In addition, the altered anatomy of the retropubic space likely plays a role, as changes in anatomical relationships (such as urethral hypermobility) are a primary factor in the problem of stress urinary incontinence.

Not wishing to be bound by any theory, it is believed that reducing the volume of retropubic fat will increase stabilization of the lower urinary tract. In addition, reducing the volume of retropubic fat may induce anterior or cephalad displacement of the lower urinary tract, thereby further improving continence. A reduction in urethral mobility alone, however, may be adequate to achieve improved continence, particularly if the position of the urethra and bladder neck are satisfactory at rest. In such instances, there may be sufficient stabilization to prevent significant movement during physical stress, thereby improving continence without the need for elevation of these structures. While the fat tissue of the retropubic space may be removed with surgical techniques, such techniques are more invasive and involve risks such as surgical bleeding during surgical dissection.

The Methods of Treatment

Accordingly, in one aspect, a method is provided for treating urinary incontinence in a patient by (1) providing a composition which includes at least one pharmaceutically active formulation capable of retropubic fat dissolution, and (2) introducing the composition into the retropubic space, to contact adjacent tissue and promote dissolution of retropubic fat therein. Introduction of the composition into the patient can be performed using a minimally invasive technique, unlike techniques for surgical removal of retropubic fat tissue. While not wishing to be bound by any theory, it is believed that the reduction or alteration of retropubic fat allows for more effective induction of adhesions, which have been shown to be an effective treatment in the stabilization of the lower urinary tract by formation of fibrous tissue attachments to fascial tissues in the retropubic area. In another embodiment, the method further includes induction of adhesions by the formation of fibrous tissue attachments to the fascial tissues in the retropubic area subsequent to the dissolution of the retropubic fat. The composition may include additional materials that facilitate or further promote the induction of adhesions.

As used herein, the term "patient" typically refers to a human being, such as an adult female human, although the methods and compositions may be adaptable to other, suitable mammalian subjects. As used herein, the term "minimally invasive" refers to surgical procedures generally performed by entering the body through the skin, a body lumen, or other anatomical structure, using small incisions, trocars, and the like, to minimize tissue trauma. Use of minimally invasive techniques can reduce operative time and anesthesia requirements, as well as postoperative pain and recovery time. In addition, elimination of the need for dissection and placement of sutures in the periurethral tissue also may reduce the possible future development of intrinsic sphincter deficiency. Thus, the present techniques have the potential to provide a minimally invasive treatment, faster recovery, improved long term results, and decreased risks and complications.

As used herein, the phrase "retropubic fat dissolution" refers to the solubilization of fat molecules, destruction of fat cell membranes, fat tissue necrosis, atrophy, reduction of fat tissue volume, and fibrosis. The term "dissolution" is used broadly to include chemical or physical degradation or decomposition, liquefaction, solubilization, dispersion, or other disruption of intact fat tissue, e.g., adipose (fat cells) specifically. Those of skill in the art will appreciate that retropubic fat dissolution as described herein does not require complete elimination of all fat tissue from the retropubic space.

As used herein, the term "retropubic space" means that region of the body that is situated posterior to the pubic bone (i.e., the region that is posterior to the pubic ramus and pubic symphysis). This is an area of loose connective tissue between the bladder with its related fascia and the pubis. The retropubic space is bounded posteriorly and inferiorly by the bladder, urethra, and endopelvic fascia (FIG. 1). The retropubic space extends upward to the rectus fascia, but does not include the supra-pubic area with the rectus fascia itself. The retropubic space does not extend beyond the sacrum.

As used herein, the phrase "endopelvic fascia" means tissue that covers the pelvic organs and surrounds vessels and nerves in the pelvic region (e.g., in the subperitoneal space).

Endopelvic fascia includes collagen, elastin, and smooth muscle. These structures surround and support the viscera in the pelvic cavity and extend from the pelvic floor to the rectus fascia and respiratory diaphragm. As used herein, endopelvic fascia can include pubocervical fascia and periurethral fascia. Endopelvic fascia also is referred to as visceral pelvic fascia.

Figure 2:
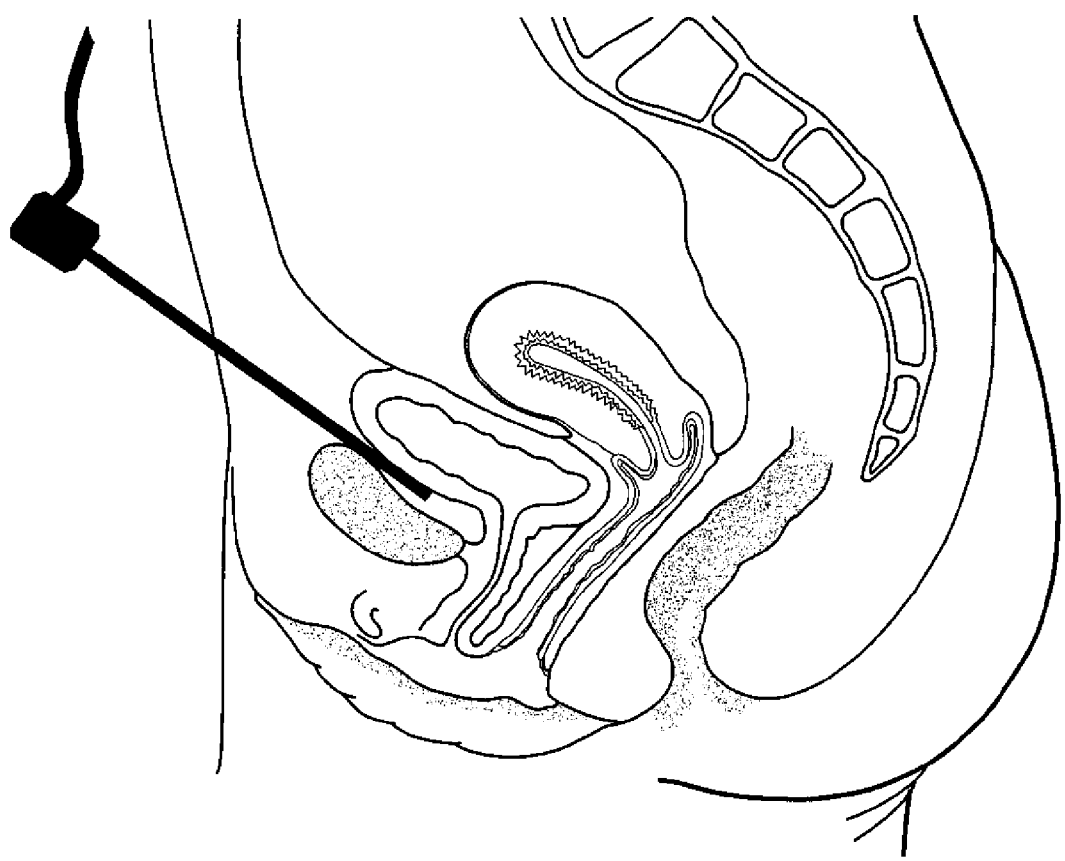
FIG. 2 is an illustration of a surgical procedure for introducing a composition into the retropubic space using endoscopic (laparoscopic) instrumentation according to a particular embodiment of the treatment method.

In a particular embodiment, the pharmaceutically active formulation is introduced into the retropubic space using minimally invasive techniques well known to those of ordinary skill in the art. In one embodiment, endoscopic (laparoscopic) instrumentation is used to provide an open space in the retropubic space and visual control for the introduction of a composition comprising at least one pharmaceutically active formulation capable of promoting dissolution of retropubic fat (illustrated in FIG. 2). Access can be achieved with small lower abdominal incisions and placement of laparoscopic trocars. This can be performed through the lower abdominal wall with direct extraperitoneal entry into the retropubic space. Alternatively, transperitoneal access to the retropubic space may be used.

Such techniques also optionally permit the use of sutures or other fastening methods to secure the composition, particularly in embodiments wherein the composition comprises a foam or fabric matrix impregnated with the at least one pharmaceutically active formulation. Endoscopic procedures also enable positioning of the tissue in a particular orientation for the stabilization of the tissue. For example, temporary sutures made of a absorbable material may be used to provide immediate stabilization of the urinary tract, thereby providing temporary support until the fat dissolution and induction of adhesions are achieved.

Figure 3:
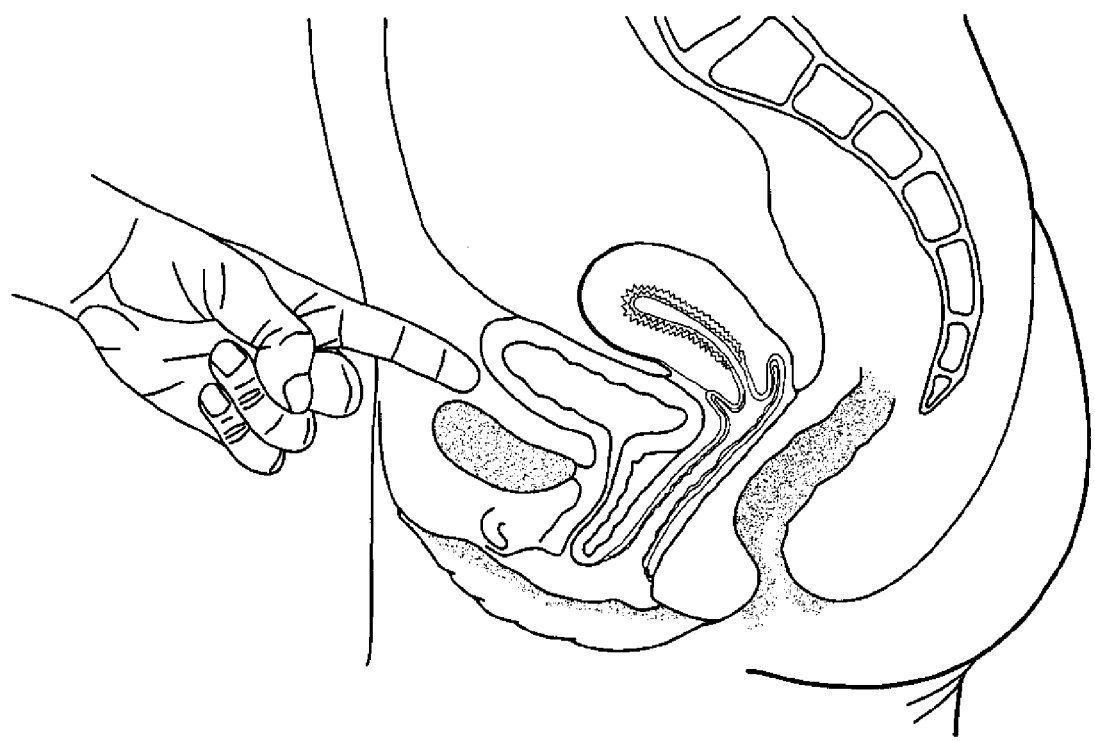
FIG. 3 is an illustration of a surgical procedure for introducing a composition into the retropubic space using minute incisions and blunt finger dissection and manual guidance according to a particular embodiment of the treatment method.

Methods of introducing the compositions also may include open surgical techniques with direct exposure to the area. For example, in a particular embodiment the composition may be introduced through minute incisions using blunt finger dissection and manual guidance (FIG. 3). The extensive dissection required for the surgical techniques of the prior art would not be needed. Thus, the current treatment may be performed using small incisions in a minimally invasive and cost-effective manner.

Figure 4:
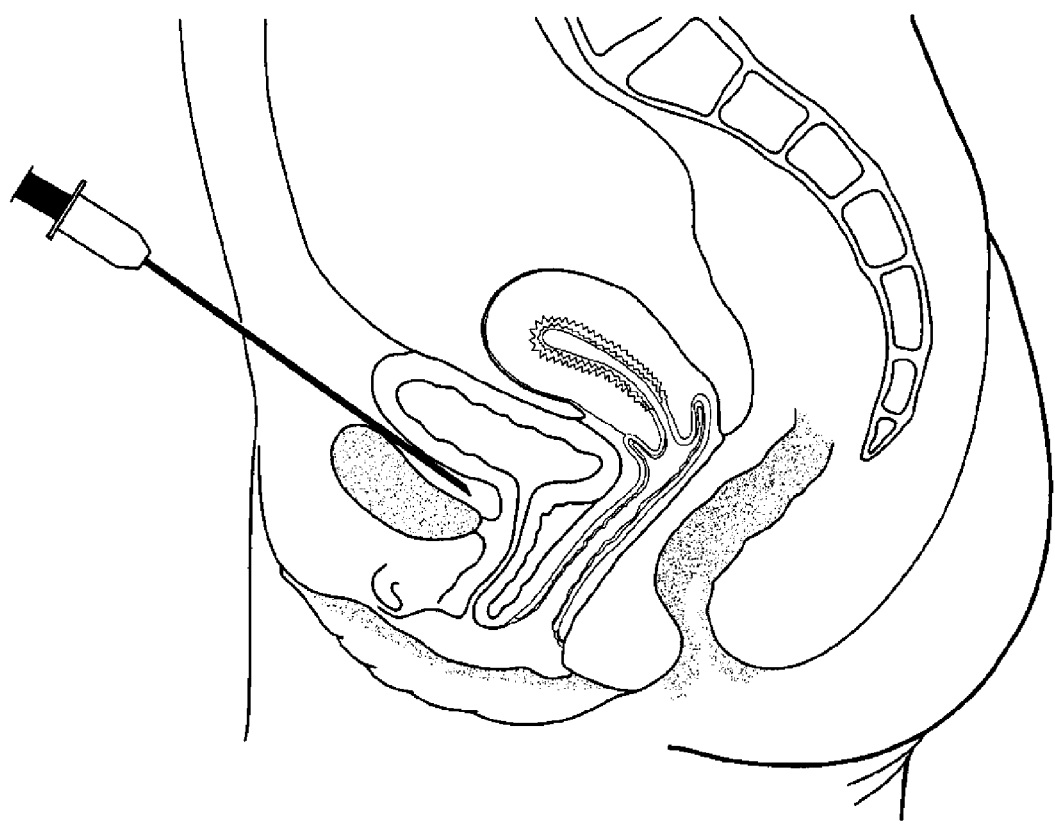
FIG. 4 is an illustration of a surgical procedure for introducing a composition into the retropubic space using a transabdominal injection according to a particular embodiment of the treatment method.
Figure 5:
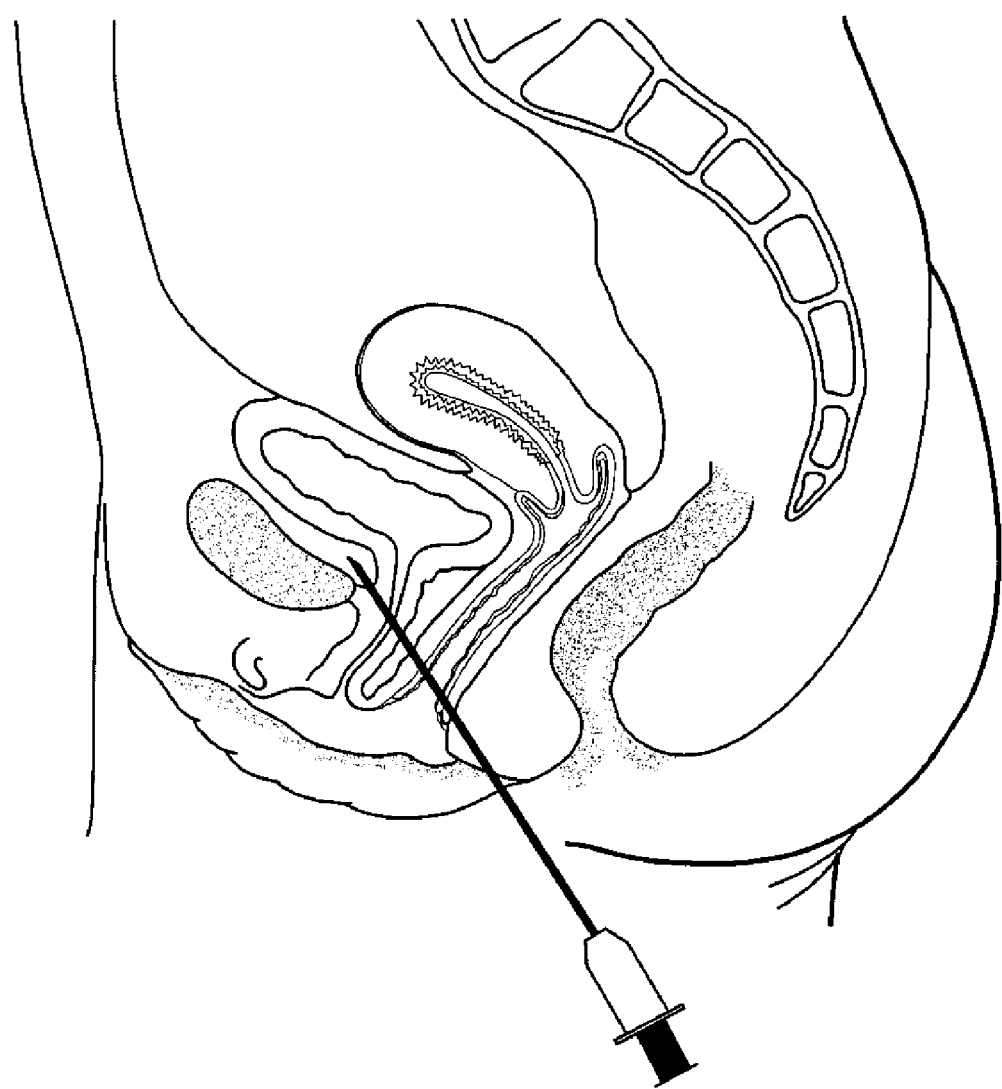
FIG. 5 is an illustration of a surgical procedure for introducing a composition into the retropubic space using a transvaginal injection according to a particular embodiment of the treatment method.

In another embodiment, the compositions may be introduced using injection methods. For example, a transabdominal injection may be performed by passing a needle just above the pubic bone and extending posteriorly and inferiorly into the retropubic space (FIG. 4). Still another method of introducing the composition includes the transvaginal introduction of the composition by puncturing the anterior vaginal wall with a needle extending anteriorly and superiorly through the endopelvic fascia to enter the retropubic space (FIG. 5).

Those of skill in the art will appreciate that imaging technologies (e.g., ultrasound, fluoroscopy, computed tomography, or magnetic resonance) may be used to facilitate delivery of the device or composition to the desired location using any of the techniques provided hereinabove.

The Compositions and Implant Devices

In another aspect, implant materials are provided for treatment of urinary incontinence. In a preferred embodiment, the implant material includes at least one pharmaceutically active formulation for promoting retropubic fat dissolution, and a biodegradable carrier material, wherein the implant material is sized and shaped, as one skilled in the art would understand, for placement within a patient's retropubic space. In a preferred embodiment, the pharmaceutically active formulation includes a pharmaceutically active detergent that is capable of causing or promoting fat dissolution. In other embodiments, the pharmaceutically active formulation includes an pharmaceutically active ingredient that is capable of causing or promoting fat dissolution, but which is not considered a detergent. Essentially any substance that destroys the retropubic fat with limited adverse effects on other tissues in the area and acceptable systemic side effects may be used.

In a particular embodiment, the pharmaceutically active formulation includes or consists of a pharmaceutically active detergent. The pharmaceutically active detergent is a biocompatible detergent suitable for in vivo retropubic fat dissolution. Representative examples of suitable detergents include ionic detergents, non-ionic detergents, zwitterionic detergents, bile acids, or combinations thereof. Non-limiting examples of bile acids include deoxycholic acid, cholic acid, chenodeoxycholic acid, 7-alpha-dehydroxylate acid, chenodeoxycholic acid, lithocholic acid, oxolithocholic acid, ursocholic acid, ursodeoxycholic acid, dihydroxy-bile acid, trihydroxy-bile acid, and their corresponding salts in either their taurine or glycine conjugate forms. A non-limiting example of an ionic detergent is sodium deoxycholate. A non-limiting example of a suitable non-ionic detergent is alkylaryl polyethyl alcohol (Triton® X-100). A non-limiting example of a suitable zwitterionic detergent includes lauryldimethylbentaine (Empigen® BB). In one embodiment, the pharmaceutically active detergent includes one or more phosphoglycerides. Representative examples of suitable phosphoglycerides include phosphatidylcholines, phosphatidylethanolamines, phosphatidylserines, phospholipid ethers, phosphatidylinositols, phosphatidylglycerols, and combinations thereof. Other suitable pharmaceutically active detergents can be readily ascertained by those skilled in the art.

In another embodiment, the pharmaceutically active formulation includes or consists of a biocompatible organic solvent (which may be an ether, an aliphatic alcohol, or acetone, for example). In still another embodiment, the pharmaceutically active formulation includes or consists of a lipase, phospholipase, sphingomyelinase (also known as a phosphodiesterase enzyme), or other enzyme. In yet another embodiment, the pharmaceutically active formulation includes or consists of an acid, a salt, or a combination of thereof, alone or with an organic solvent, lipase, or other pharmaceutically active agent.

Non-limiting examples of possible pharmaceutically active formulations for use in the present methods, compositions, and implant devices include alcohols, polyoxyethylene alkylethers, fatty acids, glycerol fatty acid esters, acetylated glycerol fatty acid esters, lower alcohol fatty acid esters, polyethylene glycol fatty acid esters, polyethylene glycol glycerol fatty acid esters, polypropylene glycol fatty acid esters, polyoxyethylene glycerides, lactic acid derivatives of mono/diglycerides, propylene glycol diglycerides, sorbitan fatty acid esters, polyoxyethylene sorbitan fatty acid esters, polyoxyethylene-polyoxypropylene block copolymers, transesterified vegetable oils, sterols, sterol derivatives, sugar esters, sugar ethers, sucroglycerids, polyoxyethylene vegetable oils, polyoxyethylene hydrogenated vegetable oils, polyoxyethylene sterols, polyoxyethylene alkylphenols, alkylglucosides, alkylmaltosides, alkylthioglucosides, lauryl macrogolglycerides, reaction mixtures of polyols and at least one member of the group consisting of fatty acids, glycerides, vegetable oils, hydrogenated vegetable oils, and sterols, tocopherol polyethylene glycol succinates, sugar esters, sugar ethers, sucroglycerides, and mixtures thereof.

The implant material desirably promotes the induction of adhesions upon the dissolution of the retropubic fat. This may be accomplished by the pharmaceutically active formulation alone or in combination with an auxiliary adhesion-promoting material. In one embodiment, the implant material further includes an adhesion-promoting material known in the art. U.S. Pat. No. 6,685,626 describes adhesion-promoting materials that promote inflammation and consequently the formation of an adhesion. Non-limiting examples of adhesion-promoting materials include fine particles of bone; fine particles of hydroxyapatite (from 1 to 1,000 micrometers particle size range); non-osteoinductive precipitated bone matrix (DBM); collagen particles intentionally partially demineralized (from 1 to 70 micrometers particle size range); collagen shards (from 1 to 70 micrometers particle size range); insoluble salts; talc; and cross-linked tissues such as gluteraldehyde. Such materials may be obtained from human tissue (e.g., cadaveric tissue) or from other sources such as bovine, ovine, or other non-human cultured species. The adhesion-promoting material desirably is non-toxic, insoluble in water, and capable of inducing a mild inflammatory response to induce fibrosis. Even more desirably, the adhesion-promoting material is biodegradable and will dissipate (e.g., biodegrade) between 7 and 30 days following introduction into a patient.

The implant material may be provided in a variety of forms. In one case, the implant material is a biodegradable, implantable medical device. The implant material may be in a particulate form (such as microcapsules, nanoparticles, and the like), a fibrous form (such as a woven or non-woven fiber material), or it may be in a unitary or monolithic structure (e.g., a porous or non-porous structure). The structure preferably is pliable and conformable to the patient's anatomical structures at the site of treatment. For example, the implant material may have a gel, paste, or putty consistency. In one embodiment, the structure may be resilient or elastic, such that it can be compressed during insertion and then expand at the implant site to secure the material at the intended location in the retropubic space. For example, the carrier material may have a sponge form, in which the pores are filled with the active agent. The implant material may be tailored to optimize local delivery of the pharmaceutically active formulation to tissues of the retropubic space. The implant material may be designed to control release of the pharmaceutically active formulation as needed to optimize fat dissolution and adhesion formation. Release may be immediate, sustained, or delayed following insertion of the material into the retropubic space. In one embodiment, the pharmaceutically active formulation is present in the implant material in an amount between about 40% and 95% by weight of the implantable material.

The biodegradable carrier material of the implant material may be provided in a variety of forms, which may or may not dictate the final form of the implantable material itself. The pharmaceutically active formulation may be coated on the biodegradable carrier material, contained within the biodegradable carrier material, dispersed within the biodegradable carrier material, or a combination thereof. The carrier material may be polymeric or non-polymeric. The term "biodegradable" is used herein with reference to the carrier material to mean that the carrier material degrades or dissolves either by enzymatic hydrolysis or exposure to water in vivo, or by surface or bulk erosion. In one embodiment, the carrier material comprises a polymer selected from poly(lactic acid), poly(glycolic acid), poly(lactic-co-glycolic acid), poly(lactide-co-glycolide), a polyethylene glycol copolymer, a polyanhydride, a poly(ortho)ester, a poly(butyric acid), a poly(valeric acid), a poly(lactide-co-caprolactone), blends, and copolymers thereof.

The implant material may further include additional bioactive or inactive ingredients. Non-limiting examples of these ingredients include any compatible combination of anti-inflammatory agents, analgesics, antimicrobial agents, dispersion agents, viscosity modifying agents, penetration enhancers, and pharmaceutically acceptable excipients known in the art. Non-limiting examples of suitable dispersion agents include hyaluronidase and collagenase. Hyaluronidase and collagenase also may facilitate healing by accelerating removal of necrotic tissue. In one particular embodiment, the implant material may further include a hemostatic substance for minimizing local bleeding at the site of site of implantation of the implantable material. Representative examples of suitable substances include a gelatin sponge, cellulose, and microfibrillar collagen.

In one embodiment, the implant material comprises or consists essentially of one or more pharmaceutically active formulations in a liquid or gel form suitable for injection via a standard gauge needle or catheter, optionally with one or more known viscosity modifying agents, pH modifying agents, osmolarity modifying agents, or combinations thereof. In one embodiment, the implant material may be inserted into the retropubic space as a solution or suspension in a suitable biocompatible liquid vehicle, such as saline.

In another embodiment, the implant material comprises an impregnated foam in which the pharmaceutically active formulation is dispersed. The impregnated foam optionally may be compressed prior to and during implantation, thereafter expanding to contact the walls and fat tissue of the retropubic space and releasing the pharmaceutically active formulation and other optional ingredients (e.g., adhesion-promoting materials).

Figure 6:
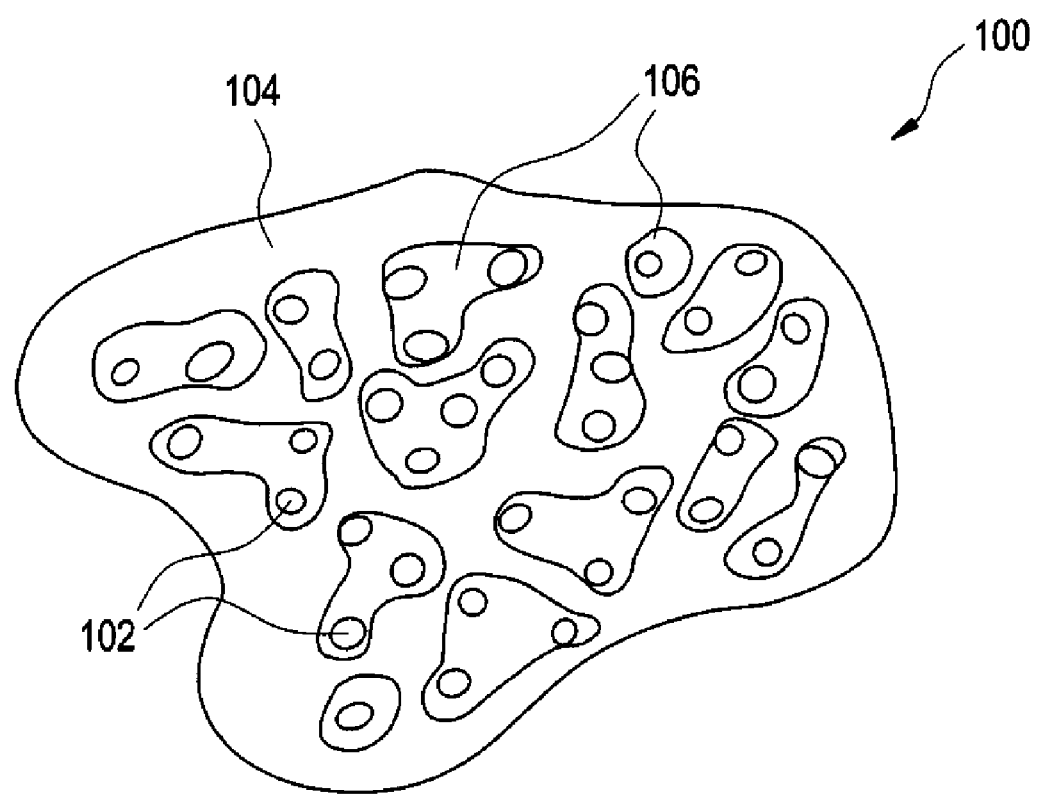
FIG. 6 is an illustration of one embodiment of an implant material as described herein.

Non-limiting examples of the implant materials are illustrated in FIG. 6 and FIG. 7A-C. FIG. 6 shows one embodiment of an implant material 100 which includes a carrier material 104 that has a plurality of pores 106 in which a pharmaceutically active detergent (or other pharmaceutically active formulation) 102 is provided for release from the pore openings at the surface of the carrier material 104.

Figure 7A:
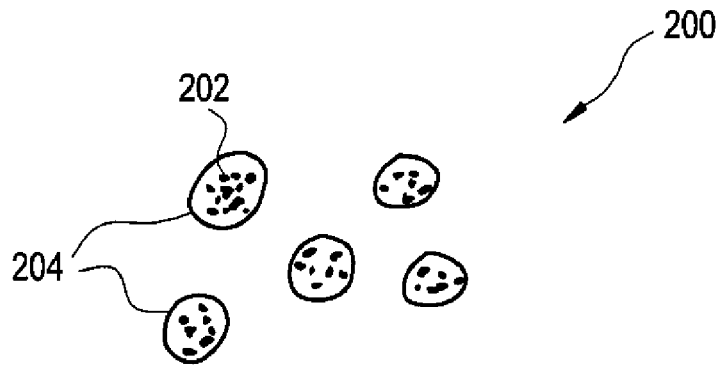
FIG. 7A-C are illustrations of other embodiments of implant materials in a particulate form (FIG. 7A), in a fibrous form (FIG. 7B), and in a resilient unitary structure (FIG. 7C).

FIG. 7A shows another embodiment of an implant material 200, which includes a collection of carrier material particles 204 in which a pharmaceutically active detergent (or other pharmaceutically active formulation) 202 is dispersed. The active agent alternatively may be encapsulated within a water soluble or biodegradable carrier material.

Figure 7B:
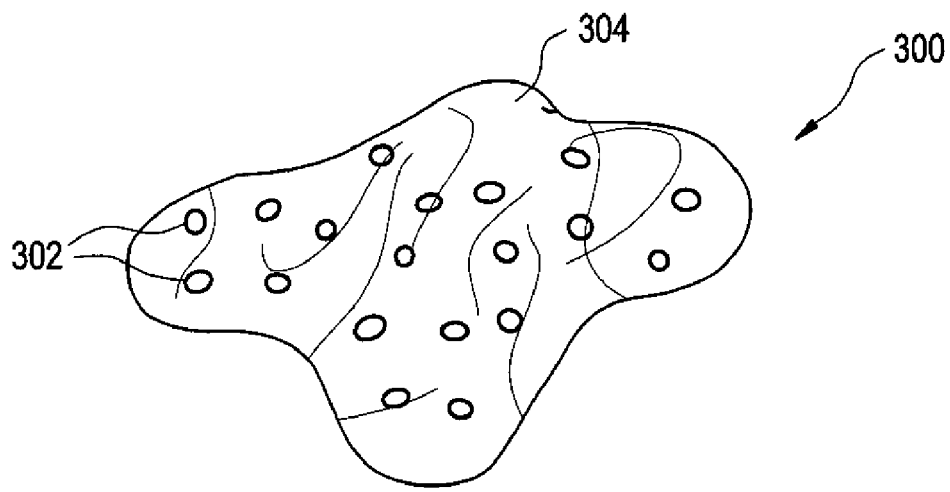

FIG. 7B shows still another embodiment of an implant material 300, that includes a fibrous carrier material 304 with which a pharmaceutically active detergent (or other pharmaceutically active formulation) 302 is loaded. The Figure shows discrete (solid or gel) particles of the active agent, but the active agent could be in a liquid form absorbed into the fibrous material or as a solid or semi-solid coating coated onto the fibrous material.

Figure 7C:
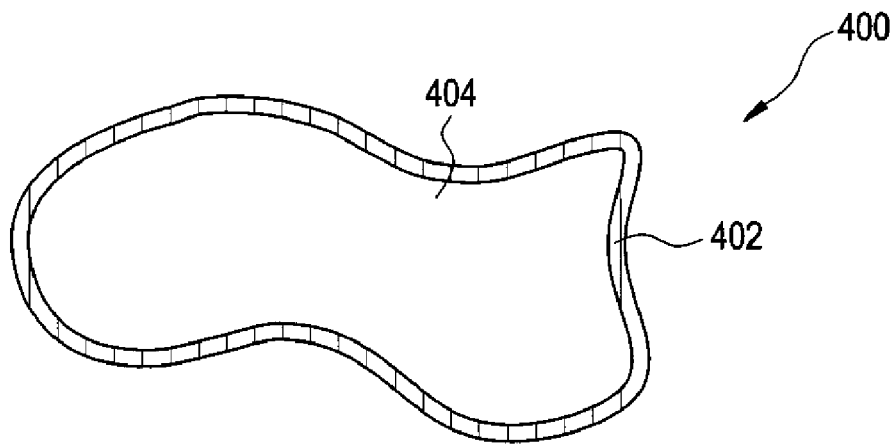

FIG. 7C shows yet another embodiment of an implant material 400 that includes a monolithic carrier material 404 that has a coating 402 that includes the pharmaceutically active detergent (or other pharmaceutically active formulation). The implant material 400 is sized and shaped for Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

I claim:

1. A method for treating urinary incontinence in a patient in need thereof comprising the steps of:
providing a composition comprising at least one pharmaceutically active formulation capable of retropubic fat dissolution; and
introducing the composition into the retropubic space of the patient, to contact adjacent tissue and promote dissolution of retropubic fat therein to treat urinary incontinence.

2. The method of claim 1, wherein the dissolution of the retropubic fat comprises solubilization of fat molecules, destruction of fat cell membranes, or a combination thereof.

3. The method of claim 1, wherein the at least one pharmaceutically active formulation comprises a pharmaceutically active detergent.

4. The method of claim 3, wherein the at least one pharmaceutically active detergent comprises a ionic detergent, a non-ionic detergent, a zwitterionic detergent, a bile acid, or a combination thereof.

5. The method of claim 3, wherein the at least one pharmaceutically active detergent comprises a bile acid selected from the group consisting of deoxycholic acid, cholic acid, chenodeoxycholic acid, 7-alpha-dehydroxylate acid, chenodeoxycholic acid, lithocholic acid, ursodeoxycholic acid, dihydroxy-bile acids, trihydroxy-bile acids, and salts thereof.

6. The method of claim 3, wherein the at least one pharmaceutically active detergent comprises at least one phosphoglyceride selected from the group consisting of phosphatidylcholines, phosphatidylethanolamines, phosphatidylserines, phospholipid ethers, phosphatidylinositols, phosphatidylglycerols, and combinations thereof.

7. The method of claim 1, wherein the at least one pharmaceutically active formulation further comprises an anti-inflammatory agent, an analgesic, a dispersing agent, a penetration enhancer, a pharmaceutically acceptable excipient, or a combination thereof.

8. The method of claim 1, wherein the composition induces the formation of adhesions in the retropubic space.

9. The method of claim 1, wherein the step of introducing the at least one pharmaceutically active formulation into the retropubic space comprises a minimally invasive procedure.

10. The method of claim 9, wherein the minimally invasive procedure comprises transvaginal, transabdominal, or transperitoneal injection.

11. The method of claim 1, wherein the composition further includes an auxiliary adhesion-promoting material selected from the group consisting of bone particles, hydroxyapatite particles, non-osteoinductive precipitated bone matrix (DBM) particles, collagen particles, insoluble salts, talc, cross-linked tissues, and combinations thereof.

12. The method of claim 1, wherein the composition comprising at least one pharmaceutically active formulation is disposed in an implant material sized and shaped for placement within the patient's retropubic space.

13. The method of claim 12, wherein the implant material further comprises a biodegradable carrier material.

14. The method of claim 13, wherein the biodegradable carrier material comprises woven or non-woven fibers.

15. The method of claim 13, wherein the biodegradable carrier material comprises a monolithic structure.

16. The method of claim 13, wherein the biodegradable carrier material comprises a sponge material.

17. The method of claim 13, wherein the pharmaceutically active formulation is coated onto the biodegradable carrier material.

18. The method of claim 13, wherein the pharmaceutically active formulation is contained within the biodegradable carrier material.

19. The method of claim 13, wherein the pharmaceutically active formulation is dispersed within the biodegradable carrier material.

20. The method of claim 1, wherein the urinary incontinence comprises stress incontinence.

* * * * *